US012521364B2

(12) United States Patent
Kim et al.

(10) Patent No.: US 12,521,364 B2

(45) Date of Patent: Jan. 13, 2026

(54) COMPOSITION FOR PREVENTING OR TREATING NEUROPATHIC PAIN, CONTAINING SYRINGARESINOL

(71) Applicant: UNIVERSITY-INDUSTRY COOPERATION GROUP OF KYUNG HEE UNIVERSITY, Gyeonggi-do (KR)

(72) Inventors: Sun Kwang Kim, Seoul (KR); Dae Sik Jang, Seoul (KR); Ik Hyun Cho, Seoul (KR); Zee Hwan Lee, Seoul (KR); Hyeonkyeong Chae, Incheon (KR); Jonghee Choi, Gyeongsangbuk-do (KR)

(73) Assignee: University-Industry Cooperation Group of Kyung Hee University, Gyeonggi-Do (KR)

( * ) Notice: Subject to any disclaimer, the term of this patent is extended or adjusted under 35 U.S.C. 154(b) by 965 days.

(21) Appl. No.: 17/762,955

(22) PCT Filed: Sep. 25, 2020

(86) PCT No.: PCT/KR2020/013091

§ 371 (c)(1),
(2) Date: Mar. 23, 2022

(87) PCT Pub. No.: WO2021/060922

PCT Pub. Date: Apr. 1, 2021

(65) Prior Publication Data

US 2022/0331285 A1 Oct. 20, 2022

(30) Foreign Application Priority Data

Sep. 25, 2019 (KR) ........................ 10-2019-0118269

(51) Int. Cl.
*A61K 31/34* (2006.01)
*A61P 25/02* (2006.01)

(52) U.S. Cl.
CPC .............. *A61K 31/34* (2013.01); *A61P 25/02* (2018.01)

(58) Field of Classification Search
CPC ...................................................... A61K 31/34
See application file for complete search history.

(56) References Cited

U.S. PATENT DOCUMENTS

| | | | | |
|---|---|---|---|---|
| 7,799,782 B2 * | 9/2010 | Munson | .................. | A61P 17/06 514/322 |
| 9,005,678 B1 | 4/2015 | Cao et al. | | |
| 10,695,394 B2 | 6/2020 | Ryu et al. | | |

FOREIGN PATENT DOCUMENTS

| | | |
|---|---|---|
| KR | 10-2004-0033983 A | 4/2004 |
| KR | 10-697212 B1 | 3/2007 |
| KR | 10-1133837 B1 | 4/2012 |
| KR | 10-1715274 B1 | 3/2017 |
| KR | 10-1800785 B1 | 11/2017 |
| KR | 10-2018-0043184 A | 8/2019 |

OTHER PUBLICATIONS

Kim et al., heterocycle, 2018, 96(5): 935-946.*

Cho et al., Neuropharmacology, 2018, 131: 68-82.*

Cho et al., ‘Syringaresinol suppresses excitatory synaptic transmission and picrotoxin-induced epileptic activity in the hippocampus through presynaptic mechanisms’, Neuropharmacology, 2018, 131, pp. 68-82.

Ki et al., “Diagnosis and Treatment of Neuropathic Pain,” J Korean Med Assoc 2008; 51(12): 1139-1148.

Kim et al., ‘The suppressive effects of Cinnamomi Cortex and its phytocompound coumarin on oxaliplatin-induced neuropathic cold allodynia in rats’, Molecules, 2016, 21,1253, pp. 1-12.

Ma et al., “Does COX2-dependent PGE2 play a role in neuropathic pain?” Neuroscience Letters 437 (2008) 165-169.

Matsunuma et al., “Oxaliplatin induces prostaglandin E2 release in vascular endothelial cells,” Cancer Chemotherapy and Pharmacology, Aug. 2019., 84(2), pp. 345-350.

Quasthoff et al., “Chemotherapy-induced peripheral neuropathy,” J. Neurol., 249:9-17, 2002.

International Search Report, Koriean Intellectual Property Office, PCT/KR2020/013091, Jan. 14, 2021.

* cited by examiner

*Primary Examiner* — Rei Tsang Shiao
(74) *Attorney, Agent, or Firm* — Gavrilovich, Dodd & Lindsey LLP

(57) ABSTRACT

The present invention relates to a composition for preventing, ameliorating, or treating neuropathic pain, comprising syringaresinol or a pharmaceutically acceptable salt thereof as an active ingredient. The composition of the present invention may be administered to a subject for which administration of an anticancer agent is scheduled or to which an anticancer agent has been administered, or to a subject which has suffered peripheral nerve damage, to thereby prevent, ameliorate, or treat neuropathic pain.

7 Claims, 4 Drawing Sheets

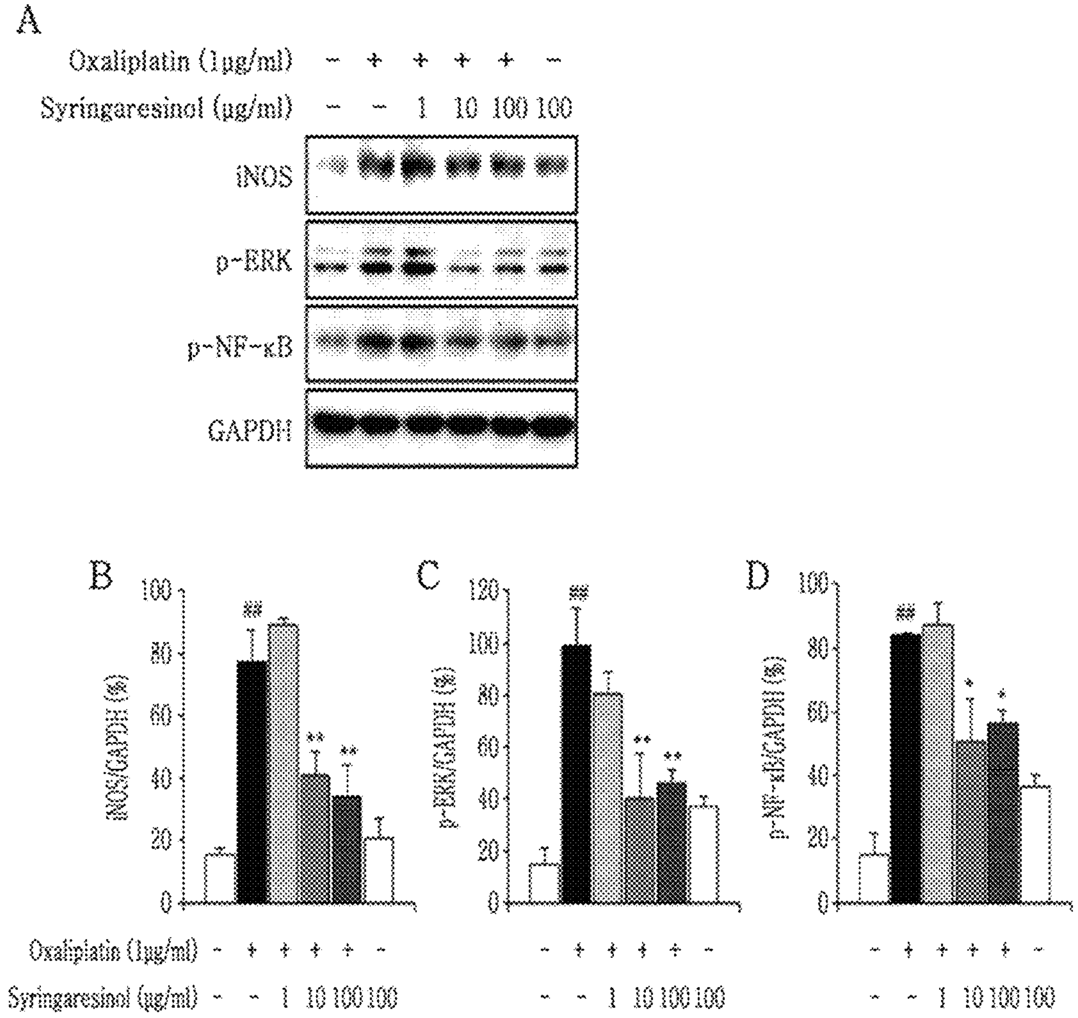
*FIG. 4A-D*

COMPOSITION FOR PREVENTING OR TREATING NEUROPATHIC PAIN, CONTAINING SYRINGARESINOL

CROSS REFERENCE TO RELATED APPLICATIONS

This application is a U.S. National Phase Application filed under 35 U.S.C. § 371 and claims priority to International Application No. PCT/KR2020/013091, filed Sep. 25, 2020, which application claims priority to Korean Patent Application No. 10-2019-0118269, filed Sep. 25, 2019, the disclosures of which are incorporated herein by reference.

TECHNICAL FIELD

The present invention relates to a composition containing syringaresinol for preventing or treating neuropathic pain.

BACKGROUND ART

Pain response is a physiological response to reduce tissue damage, and the presence of acute pain is construed to be a normal response to protect the living body. However, some pain is caused in the nervous system without appropriate stimuli to peripheral pain receptors, which is called neuropathic pain (J Korean Med Assoc 2008; 51(12):1139-1148). Neuropathic pain, once occurring, develops into very severe chronic pain due to continuous excitation resulting from the inflammatory response of pain-transmitting nerve cell bodies, structural changes of interneurons, glial cells, and synapses between the cells in the horns of the spinal cord or more, and the like.

Neuropathic pain includes spontaneous pain that occurs spontaneously even without an external stimulus, hyperalgesia in which more severe pain is caused by a stimulus that ordinarily causes pain, and allodynia in which severe pain is caused by even a weak stimulus that causes no pain. In many cases, such neuropathic pain is caused by damage to the somatosensory nervous system (peripheral nerves, etc.) or side effects resulting from chemotherapy (anticancer drugs, etc.).

There are several types of allodynia, such as pain caused by a mechanical stimulus (mechanical allodynia) and a pain caused by a cold stimulus (cold allodynia), and the degrees of occurrence of mechanical allodynia and cold allodynia may differ depending on anticancer drugs causing such allodynia (*J. Immunol.* 249:9-17, 2002). Allodynia caused by anticancer drugs, once occurring, is difficult to treat, and the pain persists for several weeks to several months and sometimes for several years, even if the use of a drug is stopped. Hence, in cases of cancer treatment using anticancer drugs, an appropriate inhibition of allodynia becomes a very important perspective in the utilization of potent anticancer effects of the drugs.

Existing analgesics (e.g., gabapentin, antidepressants, morphine, etc.) applied to neuropathic pain including allodynia are slightly effective, or even if effective, the analgesics have other side effects (e.g., dizziness, nausea, suicidal impulse, itching, etc.), and thus there is still no definitive treatment.

Various compositions for application to allodynia caused by side effects of anticancer drugs are presented in a hematopoietic promoter for treating side effects caused by anticancer drug administration, the hematopoietic promoter containing as an active ingredient a mixed herbal extract of Astragali Radix and Angelicae Gigantis Radix (Korean Patent No. 10-697212), a composition for inhibiting renal toxicity due to anticancer drug administration, the composition containing a Pulsatillae Radix extract as an active ingredient (Korean Patent No. 10-1133837), and a composition for reducing side effects due to anticancer drugs, the composition containing as an active ingredient a herbal medicine extract of Pinelliae Rhizoma and Scutellariae Radix (U.S. patent Ser. No. 10/695,394 B2). However, the inhibition of such side effects may interfere with anticancer activity of most anticancer drugs to partly reduce the anticancer activity.

Meanwhile, syringaresinol and derivatives thereof are one of the components isolated from various plants, *Cinnamomum cassia* Blume (cinnamon), *Chrysanthemum morifolium* Ramat, and edible barks, and have been known to have anticancer activity (Korean Patent Nos. 10-1715274 and 10-1800785).

DISCLOSURE

Technical Problem

The present inventors conducted intensive research efforts to contribute to the improvement in the quality of life of patients and enhance national health by developing therapy for severe pain and, as a result, identified that syringaresinol can prevent or treat neuropathic pain caused by an anticancer drug or peripheral nerve injury, thereby completing the present invention.

Technical Solution

An aspect of the present invention is to provide a pharmaceutical composition for prevention or treatment of neuropathic pain, the pharmaceutical composition containing as an active ingredient syringaresinol or a pharmaceutically acceptable salt thereof.

Another aspect of the present invention is to provide a food composition for prevention or alleviation of neuropathic pain, the food composition containing as an active ingredient syringaresinol or a food acceptable salt thereof.

Still another aspect of the present invention is to provide a method for preventing or treating neuropathic pain, the method including administering to a subject a composition containing syringaresinol or a pharmaceutically acceptable salt thereof.

Still another aspect of the present invention is to provide a kit for prevention or treatment of cancer, the kit including: a first composition containing syringaresinol or a pharmaceutically acceptable salt thereof; and a second composition containing an anticancer drug as an active ingredient.

Still another aspect of the present invention is to provide a pharmaceutical composition for prevention or treatment of cancer, the pharmaceutical composition containing: a first composition containing syringaresinol or a pharmaceutically acceptable salt thereof; and a second composition containing an anticancer drug as an active ingredient.

Still another aspect of the present invention is to provide use of a composition containing syringaresinol or a pharmaceutically acceptable salt thereof for preventing or treating neuropathic pain.

Advantageous Effects

The composition containing syringaresinol or a pharmaceutically acceptable salt thereof of the present invention is administered to a subject scheduled to receive an anticancer drug or having received an anticancer drug and thus can prevent, alleviate, or treat allodynia.

BRIEF DESCRIPTION OF DRAWINGS

FIG. 4A-D shows the effects of syringaresinol on cells with an inflammatory response induced by oxaliplatin. A: Protein bands (iNOS, p-ERK, and p-NF-κB) by Western blot assay, B-D: Quantification graphs of A (B: iNOS, C: p-ERK, and D: p-NF-κB).

DETAILED DESCRIPTION OF THE INVENTION

Figure 1:
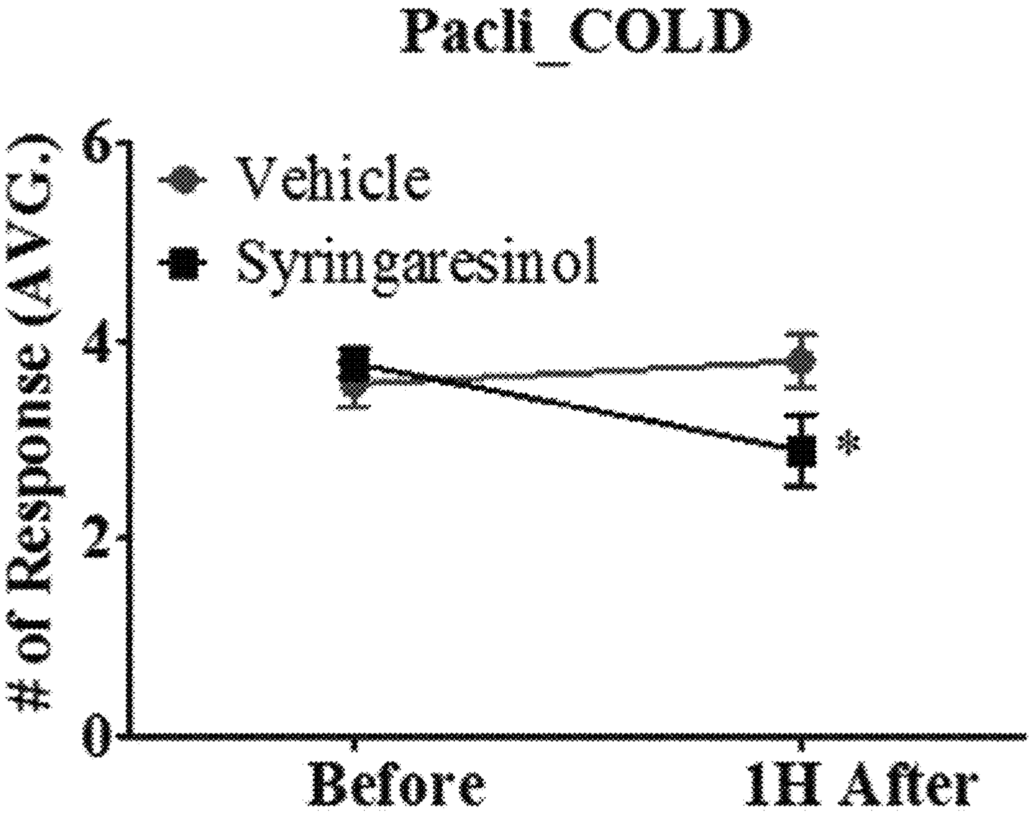
FIG. 1 shows the results of orally administering syringaresinol to an experimental group with neuropathic pain caused by oxaliplatin.

The present invention will be specifically described as follows. Each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description below.

Hereinafter, the present invention will be described in more detail. Each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description below. Furthermore, those skilled in the art will recognize or be able to ascertain, using no more than routine experimentation, many equivalents to the specific embodiments of the invention described herein. Further, these equivalents should be interpreted to fall within the scope of the present invention.

In accordance with an aspect of the present invention, there is provided a pharmaceutical composition for prevention or treatment of neuropathic pain, the pharmaceutical composition including as an active ingredient syringaresinol or a pharmaceutically acceptable salt thereof.

As used herein, the term "syringaresinol" refers to a compound represented by Chemical Formula 1 below, which is one of the components of cinnamon.

[Chemical Formula 1]

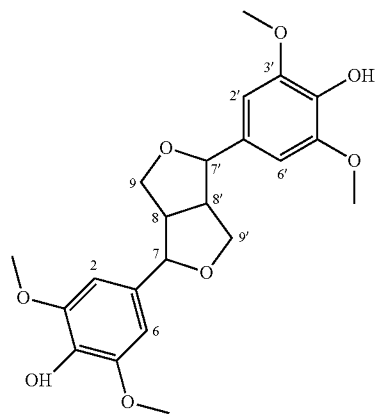

Cinnamon, a raw material of syringaresinol, refers to the bark of *Cinnamomum cassia* of the family Lauraceae or other closely related plants of the same genus. Traditionally, in the oriental medicine, cinnamon has been known to have efficacy of removing fever, blood circulation, keeping up energy, and the like. Many studies of such cinnamon have been conducted on an action on the nerves, immune and anti-cancer actions, an antibacterial action, and the like, and cinnamon has been traditionally used for prescriptions for ongyeongtang, gyejitang, gyejiboknyeonghwan, sogeonjungtang, and socheongnyongtang.

Cinnamon with the above-described characteristics is a widely used herbal medicine, and when the cinnamon is applied to the human body, side effects rarely occur, and syringaresinol, which is a component of cinnamon, may also be used without side effects.

The syringaresinol may be purchased and used in a form that is already commercially available, and may be used in a form that is extracted and purified from herbal medicines, such as cinnamon, by methods known in the art, or may be chemically synthesized.

In the present invention, the syringaresinol has uses of preventing or treating neuropathic pain.

The syringaresinol having the aforementioned uses includes any pharmaceutically acceptable forms, such as a salt, an isomer, an ester, an amide, a thioester, and a solvate, but is not limited thereto.

The pharmaceutically acceptable salts of syringaresinol mean salts prepared by way of ordinary methods in the art, and such preparation methods are known to those skilled in the art. Specifically, the pharmaceutically acceptable salts include pharmacologically or physiologically acceptable salts derived from the following inorganic acids, organic acids, and bases, but are not limited thereto.

An acid addition salt is prepared by way of an ordinary method, for example, by dissolving a compound in an excess of an acid aqueous solution and precipitating this salt using a water-miscible organic solvent, such as methanol, ethanol, acetone, or acetonitrile. Equimolar amounts of a compound and an acid or alcohol (e.g., glycol monomethyl ether) in water are heated, and then the mixture may be dried by evaporation, or the precipitated salt may be subjected to suction filtration. Organic acids and inorganic acids may be used as free acids. Examples of the inorganic acids may include hydrochloric acid, phosphoric acid, sulfuric acid, nitric acid, tartaric acid, and the like, and examples of the organic acids may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like, but are not limited thereto.

The bases may also be used to prepare pharmaceutically acceptable metal salts. An alkali metal or alkaline earth metal salt is, for example, obtained by dissolving a compound in an excess of an alkali metal hydroxide or alkali earth metal hydroxide solution, filtering out a non-solubilized compound salt, and then evaporating and drying the filtrate. In particular, the preparation of a sodium, potassium, or calcium salt as a metal salt is pharmaceutically appropriate, but is not limited thereto. A silver salt corresponding thereto may be obtained by reaction of an alkali metal or alkaline earth metal salt with an appropriate silver salt (e.g., silver nitrate).

As used herein, the term "neuropathic pain" refers to a pain condition that is caused in the nervous system without an appropriate stimulus to a peripheral pain receptor, and the main cause thereof is damage to the somatosensory nervous system including peripheral nerves and the like or side effects of chemotherapy using an anticancer drug and the like.

In the present invention, the neuropathic pain is allodynia caused by an anticancer drug or a pain caused by peripheral nerve injury, but is not limited thereto.

As used herein, the term "allodynia" refers to a condition, symptom, or disease that causes severe pain due to even a weak stimulus causing no pain in a normal state, wherein allodynia is included as one of the neuropathic pain. There are several types of allodynia, such as pain caused by a mechanical stimulus (mechanical allodynia) and pain caused by a cold stimulus (cold allodynia), and the degrees of occurrence of mechanical allodynia and cold allodynia may differ depending on the anticancer drug.

As used herein, the term "anticancer drug" refers to a prophylactic and therapeutic agent for cancer, and examples of the anticancer drug include prophylactic and therapeutic agents for cancer that cause peripheral nerve disorders as side effects, such as lung cancer (e.g., non-small cell lung cancer, small cell lung cancer, and malignant mesothelioma), mesothelioma, pancreatic cancer (e.g., pancreatic duct cancer and pancreatic endocrine tumor), pharyngeal cancer, laryngeal cancer, esophageal cancer, gastric cancer (e.g., papillary adenocarcinoma, mucous adenocarcinoma, and glandular squamous cell carcinoma), duodenal cancer, small intestine cancer, colon cancer (e.g., colon cancer, rectal cancer, anal cancer, familial colon cancer, hereditary colon cancer, hereditary nonpolyposis colorectal cancer, and gastrointestinal interstitial tumor), breast cancer (e.g., invasive ductal cancer, non-invasive ductal cancer, and inflammatory breast cancer), ovarian cancer (e.g., epithelial ovarian carcinoma, extra-testicular germ cell tumor, ovarian germ cell tumor, and ovarian low malignant potential tumor), testicular tumor, prostate cancer (e.g., hormone-dependent prostate cancer and hormone-independent prostate cancer), liver cancer (e.g., hepatocellular carcinoma, primary liver cancer, and extrahepatic bile duct cancer), thyroid cancer (e.g., medullary thyroid carcinoma), kidney cancer (e.g., renal cell carcinoma and transitional epithelial carcinoma of the renal pelvis and ureter), cervical cancer (e.g., cervical cancer, uterine body cancer, and uterine sarcoma), brain tumors (e.g., medulloblastoma, glioma, pineal gonadoblastoma, spheroid gonadocytoma, diffuse gonadoblastoma, degenerative gonadoblastoma, and pituitary adenoma), retinoblastoma, skin cancer (e.g., basal cell carcinoma and malignant melanoma), sarcoma (e.g., rhabdomyosarcoma, leiomyosarcoma, and soft tissue sarcoma), malignant bone tumor, bladder cancer, blood cancer (e.g., multiple myeloma, leukemia, malignant lymphoma, Hodgkin's disease, and chronic myelogenous disease), primary unknown cancer, and the like.

Examples of these anticancer drugs may include taxane-based anticancer drugs (e.g., paclitaxel (taxol) and docetaxel), *vinca* alkaloid anticancer drugs (e.g., vincristine and vinblastine), platinum-based agents (e.g., cisplatin, carboplatin, and oxaliplatin), molecular targeted drugs (e.g., bortezomib), and the like, specifically at least one anticancer drug from taxane- or platinum-based agents, and more specifically at least one of paclitaxel or oxaliplatin, but are not limited thereto.

Among the aforementioned anticancer drugs, paclitaxel, oxaliplatin, vincristine, cisplatin, carboplatin, and bortezomib are known to cause the side effect allodynia, which is neuropathic pain (*J. Clin Oncol.* 24:1633-1642, 2006; *Neurotoxicology,* 27:992-1002, 2006; and *British Journal of Haematology,* 127, 165-172, 2004).

The pharmaceutical composition of the present invention has uses of "preventing" and/or "treating" neuropathic pain. For uses of prevention, the pharmaceutical composition of the present invention is administered to a subject having or suspected of being at risk of developing the diseases, disorders, or conditions described herein. That is, the pharmaceutical composition of the present invention may be administered to a subject scheduled to receive an anticancer drug, at risk of developing allodynia due to the administration of an anticancer drug, or (at risk of) developing neuropathic pain due to peripheral nerve injury. For uses of treatment, the pharmaceutical composition of the present invention is administered to a subject, such as a patient who has already suffered from the disorders described herein, in an amount sufficient to treat or at least partly stop the symptoms of the diseases, disorders, or conditions described herein. The amount effective for these uses may vary depending on the severity and progress of a disease, disorder, or condition, the previous treatment, the health condition and drug responsiveness of a subject, and the judgment of a physician or a veterinarian.

Suitable carriers, excipients, or diluents that are commonly used in the preparation of the pharmaceutical composition of the present invention may be further contained. The content of the compound above contained in the composition may include, but is not particularly limited to, 0.0001 wt % to 10 wt %, and preferably 0.001 wt % to 1 wt %, relative to the total weight of the composition.

The pharmaceutical composition may have any one formulation selected from the group consisting of a tablet, pills, a powder, granules, a capsule, a suspension, an oral liquid preparation, an emulsion, a syrup, a sterile aqueous solution, a non-aqueous solvent, a lyophilized preparation, and a suppository, and may have several oral or parenteral formulations. Specifically, the pharmaceutical composition, when formulated as a preparation, may be formulated using a diluent or an excipient, such as a filler, an extender, a binder, a wetting agent, a disintegrant, or a surfactant, which are commonly used. Exemplary solid preparations for oral administration include a tablet, pills, a powder, granules, a capsule, and the like, and such solid preparations may be prepared by mixing at least one compound with at least one excipient, for example, starch, sucrose, lactose, gelatin, or the like. Besides simple excipients, lubricants, such as magnesium stearate and talc, may be used. Exemplary liquid preparations for oral administration correspond to a suspension, an oral liquid preparation, an emulsion, a syrup, and the like, and may contain simple diluents that are frequently used, such as water and liquid paraffin, as well as several types of excipients, such as a wetting agent, a sweetening agent, a flavoring agent, and a preservative. Exemplary preparations for parenteral administration include a sterile aqueous solution, a non-aqueous solvent, a suspension, an emulsion, a lyophilized preparation, and a suppository. Examples of the non-aqueous solvent and the suspension may include propylene glycol, polyethylene glycol, a vegetable oil such as olive oil, an injectable ester such as ethylolate, and the like. Examples of a base material for the suppository may include Witepsol, Macrogol, Tween 61, cocoa butter, laurin butter, glycerogelatin, and the like.

The pharmaceutical composition of the present invention may be administered to a subject in a pharmaceutically effective amount.

As used herein, the term "pharmaceutically effective amount" refers to an amount sufficient to treat a disease at a reasonable benefit/risk ratio applicable to medical treatment, and the level of the effective dose may be determined depending on factors including the type of subject, the severity of disease, age, sex, type of disease, drug activity, drug sensitivity, time of administration, route of administration, rate of excretion, duration of treatment, and a drug to be used in combination, and other factors well known in the medical field. The composition of the present invention may be administered as an individual therapeutic agent or in combination with other therapeutic agents, and may be sequentially or simultaneously administered together with a conventional therapeutic agent. In addition, the pharmaceutical composition may be administered once or multiple times. It is important to administer the pharmaceutical composition in an amount to obtain the maximum effect with a minimum amount and without side effects considering all of the factors described above, and such an amount may be easily determined by those skilled in the art. The preferred dose of the composition of the present invention varies depending on the patient's condition and body weight, the severity of disease, the form of drug, and route and duration of administration, and the composition of the present invention may be administered once or several times in divided doses per day. The composition can be applied to any subject, without particular limitation, as long as the pharmaceutical composition has a purpose of preventing or treating neuropathic pain of the subject. Any manner of administration is included, without limitation, as long as the manner is commonly used in the art. For example, administration may be conducted by oral, intraperitoneal, rectal, intravenous, intramuscular, subcutaneous, intrauterine dural, or intracerebrovascular injection.

The pharmaceutical composition of the present invention may be orally administered at a concentration of 5 mg/kg to 100 mg/kg and, specifically 5 mg/kg to 50 mg/kg, but is not limited thereto.

According to an exemplary embodiment of the present invention, 10 mg/kg syringaresinol was orally administered to animal models with allodynia induced by paclitaxel or oxaliplatin, and as a result, it was identified that cold allodynia due to paclitaxel and cold allodynia and mechanical allodynia due to oxaliplatin were mitigated. According to another exemplary embodiment of the present invention, 10 mg/kg syringaresinol was orally administered to animal models with neuropathic pain induced by peripheral nerve injury, and as a result, it was identified that mechanical pain was mitigated.

That is, the syringaresinol or pharmaceutically acceptable salt thereof of the present invention is administered to a subject with allodynia due to an anticancer drug or neuropathic pain due to peripheral nerve injury and thus can prevent the occurrence of pain or mitigate the degree of occurrence thereof.

In addition, according to an exemplary embodiment of the present invention, microglia with an inflammatory response induced by oxaliplatin were treated with syringaresinol at different concentrations (1 μg/mL, 10 μg/mL, and 100 μg/mL), and as a result, it was identified that the inflammatory response caused by oxaliplatin was inhibited by significantly inhibiting the protein expression of iNOS, a representative enzyme involved in the inflammatory response and significantly inhibiting the protein expression of p-ERK MAPK and p-NF-κB in the signaling mechanisms of ERK and NF-κB, which are major signaling mechanisms involved in the inflammatory response.

That is, the syringaresinol or pharmaceutically acceptable salt thereof of the present invention can inhibit the inflammatory response caused by an anticancer drug, thereby preventing the occurrence of pain or mitigating the degree of occurrence thereof, in neuroglia including microglia that perform homeostasis maintenance and defensive functions in the central nervous system.

For the purposes of the present invention, the syringaresinol or pharmaceutically acceptable salt thereof can not only minimize side effects by mitigating allodynia due to the anticancer drug, but also maximize anticancer activity by administration in combination with the anticancer drug. That is, the administration of an anticancer drug in combination with syringaresinol or a pharmaceutically acceptable salt thereof can enhance anticancer activity compared with the administration of the anticancer drug alone.

In accordance with another aspect of the present invention, there is provided a food composition for prevention or alleviation of neuropathic pain, the food composition containing as an active ingredient syringaresinol or a food acceptable salt thereof.

The terms used herein are as described above.

As used herein, the "alleviation" refers to any action that alleviates or advantageously changes symptoms of a subject having or suspected of having neuropathic pain by using a composition containing as an active ingredient syringaresinol or a food acceptable salt thereof.

As the food acceptable salt of the present invention, an acid addition salt formed by a food acceptable free acid or a metal salt formed by a food acceptable base is useful. As one example, an inorganic acid and an organic acid may be used as the free acid. Examples of the inorganic acid may include hydrochloric acid, sulfuric acid, bromic acid, sulfurous acid, or phosphoric acid, and examples of the organic acid may include citric acid, acetic acid, maleic acid, fumaric acid, gluconic acid, methanesulfonic acid, and the like. Examples of the metal salt may include an alkali metal salt or an alkaline earth metal salt, such as a sodium, potassium, or calcium salt. However, these are not necessarily limited thereto.

The food composition for prevention or alleviation of neuropathic pain of the present invention includes forms of pills, a powder, granules, an infusion, a tablet, a capsule, a liquid preparation, or the like, and exemplary foods, to which the composition of the present invention can be added, include various kinds of foods, for example, beverages, gums, teas, vitamin complexes, and health supplement foods.

As essential ingredients that may be contained in the food composition of the present invention, other ingredients than those containing the compound represented by Chemical Formula 1 above are not particularly limited, and various herbal extracts, food supplement additives, or natural carbohydrates may be contained as additional ingredients, like in ordinary foods. In the food composition, the amounts of the essential ingredients mixed may be appropriately determined according to the purpose of use (prevention, alleviation, health, or therapeutic treatment).

Examples of the food supplement additives include food supplement additives that are commonly used in the art, for example, a flavoring agent, a savoring agent, a coloring agent, a filler, a stabilizer, and the like.

Examples of the natural carbohydrates may include: ordinary sugars, for example, monosaccharides, such as glucose and fructose, disaccharides, such as maltose and sucrose, and polysaccharides, such as dextrin and cyclodextrin; and sugar alcohols, such as xylitol, sorbitol, and erythritol. Besides the above-described ones, natural flavoring agents (e.g., rebaudioside A, glycyrrhizin, etc.) and synthetic flavoring agents (saccharin, aspartame, etc.) may be advantageously used as the flavoring agent.

Additionally, the food composition of the present invention may contain various nutrients, vitamins, minerals (electrolytes), flavoring agents, such as synthetic flavoring agents and natural flavoring agents, coloring agents, fillers (cheese, chocolate, etc.), pectic acid and salts thereof, alginic acid and salts thereof, organic acids, protective colloidal thickeners, pH adjusters, stabilizers, preservatives, glycerin, alcohol, carbonating agents used for carbonated drink, and the like. Above these, the food composition of the present invention may contain fruit flesh for manufacturing natural fruit juice, fruit juice drinks, and vegetable drinks. These ingredients may be used either alone or in combination.

In the present invention, examples of the health supplement food include a health functional food, a health food, and the like. The functional food, which is the same term as food for special health use (FoSHU), refers to a food with high medicinal and medical effects to efficiently exhibit a bio-regulatory function in addition to a function of nutrient supply. The term "functional" refers to controlling nutrients for the structure or functions of the human body or providing beneficial effects to health purposes, such as physiological effects. The food of the present invention may be manufactured by a method that is commonly used in the art, and in the manufacturing of the food, the food may be manufactured by adding raw materials and ingredients that are commonly added in the art. In addition, the food may be manufactured in any formulation, without limitation, as long as the formulation is acceptable as a food. The food composition of the present invention may be prepared in various formulations, and unlike ordinary medicines, the food composition has an advantage that there is no side effect that may occur when a drug is taken for a long time, because of using the food as a raw material, and has excellent portability.

In accordance with still another aspect of the present invention, there is provided a method for preventing or treating neuropathic pain, the method including administering to a subject a composition containing syringaresinol or a pharmaceutically acceptable salt thereof.

The terms used herein are as described above.

As used herein, the term "subject" refers to any animal that is scheduled to receive an anticancer drug, had or is likely to develop allodynia due to the administration of an anticancer drug, or had or is likely to develop neuropathic pain due to peripheral nerve injury, and the subject can be efficiently treated by administering the pharmaceutical composition of the present invention to a subject suspected of having neuropathic pain.

As used herein, the term "administration" refers to an introduction of the pharmaceutical composition of the present invention into a subject suspected of having neuropathic pain by any suitable method, and the composition of the present invention may be administered through various oral or parenteral routes as long as the composition can reach a target tissue.

The pharmaceutical composition of the present invention may be administered at a pharmaceutically effective amount, and the pharmaceutically effective amount is as described above.

The pharmaceutical composition of the present invention can be applied to any subject, without particular limitation, as long as the pharmaceutical composition has a purpose of preventing or treating neuropathic pain of the subject. For example, the pharmaceutical composition may be applied to any non-human animals, such as monkeys, dogs, cats, rabbits, marmots, rats, mice, cows, sheep, pigs, and goats, and birds and fish. The pharmaceutical composition is administered through parenteral, subcutaneous, intraperitoneal, intrapulmonary, and intranasal routes, and for topical treatment, if necessary, the pharmaceutical composition may be administered by way of any suitable method including intralesional administration. A suitable dose of the pharmaceutical composition of the present invention may vary depending on the condition and body weight of a subject, the severity of disease, the form of drug, and the manner and period of administration, but may be appropriately selected by those skilled in the art. For example, administration may be conducted by oral, intraperitoneal, rectal, intravenous, intramuscular, subcutaneous, intrauterine dural, or intracerebrovascular injection, but is not limited thereto.

A suitable total daily dose may be determined by a care physician within the scope of correct medical judgment, and generally, 0.001 mg/kg to 1000 mg/kg, specifically 0.05 mg/kg to 1000 mg/kg, and more specifically 5 mg/kg to 100 mg/kg may be administered once or several times in divided doses per day.

In accordance with still another aspect of the present invention, there is provided a kit for prevention or treatment of cancer, the kit including: a first composition containing syringaresinol or a pharmaceutically acceptable salt thereof; and a second composition containing an anticancer drug as an active ingredient.

The terms used herein are as described above.

The kit of the present invention refers to a tool that contains the first composition and the second composition and thus can be used for prevention or treatment of cancer. The kit is not particularly limited to the type thereof, and a kit in the form that is commonly used in the art may be used.

The kit of the present invention may be packaged in the form in which the first composition and the second composition are separately contained in individual containers, or contained in one container divided into one or more compartments, and the first composition and the second composition each may be packaged in a unit dosage form of a single dose.

The first composition and the second composition in the kit may be separately administered in combination at the appropriate time according to the health condition of a subject to be administered. The routes and frequencies of the first composition and the second composition may each be independent.

The kit of the present invention may further include an instruction manual describing a dose, a method of administration, and a frequency of administration for each of the first and second compositions.

In accordance with still another aspect of the present invention, there is provided a method for preventing or treating cancer by using the kit.

The terms used herein are as described as above.

In accordance with still another aspect of the present invention, there is provided a pharmaceutical composition for prevention or treatment of cancer, the pharmaceutical composition containing: a first composition containing syringaresinol or a pharmaceutically acceptable salt thereof; and a second composition containing an anticancer drug as an active ingredient.

The terms used herein are as described above.

In accordance with still another aspect of the present invention, there is provided use of a composition containing syringaresinol or a pharmaceutically acceptable salt thereof for preventing or treating neuropathic pain.

The terms used herein are as described above.

MODE FOR CARRYING OUT THE INVENTION

Hereinafter, the configuration and effects of the present invention will be described in more detail with reference to exemplary embodiments. However, these exemplary embodiments are for illustrative purposes only, and the scope of the present invention is not intended to be limited by these exemplary embodiments.

Example 1: Preparation of Composition Containing Syringaresinol

Syringaresinol was dissolved in a 0.06% Tween 80 solution to a concentration of 1 mg/mL.

Example 2: Verification of Effects of Syringaresinol on Mitigation of Paclitaxel-Induced Neuropathic Pain Paclitaxel (Sigma-Aldrich) dissolved in a 1:1 solution of Cremophor EL and ethanol at 6 mg/mL was diluted to a concentration of 0.2 mg/mL, and 2 mg/kg of the diluent was intraperitoneally administered to ten 6-week-old c57/bl6 male mice four times. Injections were conducted on days 0, 2, 4, and 6 at intervals of every other day. A significant pain was observed from about 10 days after the first injection.

In the paclitaxel-induced neuropathic pain animal models, the response occurring after about 20 μL of acetone was applied to both rear paws of the animal models to cause cold allodynia was observed and recorded for about 15 seconds. The behaviors of withdrawal, shaking, and licking of the paws were observed and recorded. A total of three repeated trials were performed, and the average number of behaviors recorded was checked.

On the 14th day after the first injection of paclitaxel, animal models showing a statistically significant level of pain were divided into a drug group administered 10 mg/kg of syringaresinol (syringaresinol, n=5) and a control group orally administered 0.06% Tween 80 (vehicle, n=5), and then were administered the corresponding drugs to thereby cause cold allodynia after 1 hour.

As a result, it was identified in FIG. 1 that cold allodynia was mitigated in the group orally administered syringaresinol compared with the control group (vehicle).

Example 3: Verification of Effects of Syringaresinol on Mitigation of Oxaliplatin-Induced Neuropathic Pain Oxaliplatin (Sigma-Aldrich) dissolved in a 5% glucose solution to 2 mg/mL was single-intraperitoneally administered at 6 mg/kg to twelve 5-week-old c57/bl6 male mice. Significant pain was observed from about 3 days after the first injection.

Cold allodynia was caused in the oxaliplatin-induced neuropathic pain animal models by way of the method in Example 2.

The behavior of withdrawal to a stimulus using a 0.4 g von Frey filament (Touch test 3.61, Stoelting, USA), which causes mechanical allodynia in the oxaliplatin-induced neuropathic pain animal models, was recorded and observed. To measure the withdrawal response of the paws in the animal models, the animals were put in a transparent acrylic box (7 cm×10 cm) placed on a wire mesh with a grid size of 5 mm and given time to acclimate to the environment. After about 1 hour, the acclimation of the mice was checked, and the medial part of the affected paw was stimulated with the quantified von Frey filament through a wire mesh grid. A total of 10 stimulations sufficient to slightly bend the von Frey filament were given at intervals of 20 seconds, and the number of withdrawals was measured.

On the 3rd day after the oxaliplatin injection, animal models showing a statistically significant level of pain were divided into a drug group administered 10 mg/kg syringaresinol (syringaresinol, n=6) and a control group orally administered 0.06% Tween 80 (vehicle, n=6), and then were administered the corresponding drugs to thereby cause cold allodynia and mechanical allodynia after 1 hour.

Figure 2:
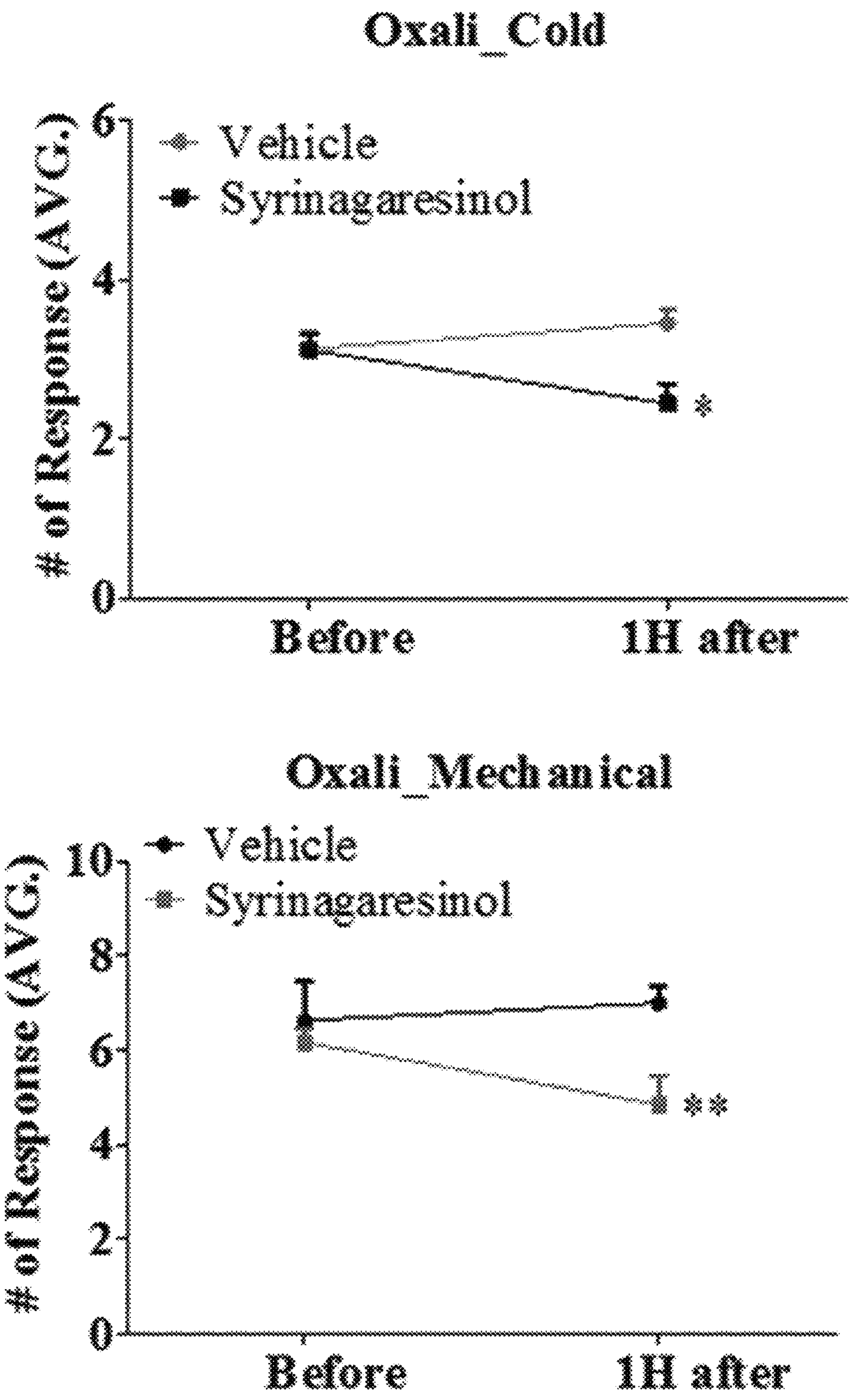
FIG. 2 shows the results of orally administering syringaresinol to an experimental group with neuropathic pain caused by paclitaxel. Top: results with respect cold allodynia, Bottom: results with respect to mechanical allodynia

As a result, it was identified in FIG. 2 that cold allodynia and mechanical allodynia were mitigated in the group orally administered syringaresinol compared with the control group (vehicle).

Example 4: Verification of Effects of Syringaresinol on Mitigation of Peripheral Nerve Injury (Partial Sciatic Nerve Ligation, PNL)-Induced Neuropathic Pain After twelve 5-week-old c57/bl6 male mice were respiratory anesthetized with 2.5% isoflurane, the skin on the posterior side of the right hip joint was shaved and incised, and then the sciatic nerve between the biceps femoris was found and confirmed. Thereafter, the median nerve was penetrated and ligated by a 7 m/m (3/8) silk thread, and then the cut skin was sutured. The neuropathic pain was caused in the animal models, and then the animal models were divided into a drug group administered 10 mg/kg of syringaresinol (syringaresinol, n=8) and a control group orally administered 0.06% Tween 80 (vehicle, n=4), and then mechanical pain was caused by way of the method in Example 3.

Figure 3:
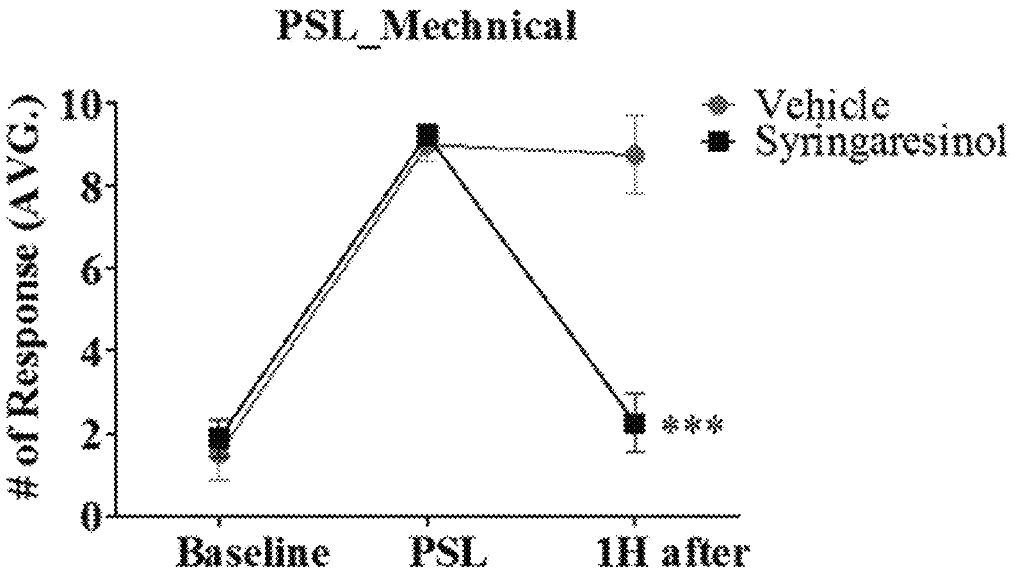
FIG. 3 shows the results of orally administering syringaresinol to an experimental group with neuropathic pain caused by peripheral nerve injury.

As a result, it was identified in FIG. 3 that mechanical pain was significantly mitigated in the group orally administered syringaresinol compared with the control group (vehicle).

Example 5: Verification of Effects of Syringaresinol on Oxaliplatin-Induced Inflammatory Response BV2 cell lines (microglia) were cultured in Dulbecco's modified Eagle's medium (DMEM; GIBCO, Grand Island, NY, USA) containing 10% fetal bovine serum (FBS; GIBCO) and 1% penicillin in a 5% $CO_2$ incubator (37° C.).

To investigate the effect of syringaresinol on the oxaliplatin-induced inflammatory response activated in the BV2 cells, the cultured BV2 cells were placed at $5\times10^5$ in 6-well plates, and then were divided into a normal control group (Nor group) treated with neither oxaliplatin nor syringaresinol, a group having an oxaliplatin-induced inflammatory response (oxaliplatin group), a group having an oxaliplatin-induced inflammatory response and treated with syringaresinol (oxaliplatin and syringaresinol group), and a group in which normal cells having no oxaliplatin-induced inflammatory response were treated with syringaresinol (syringaresinol group). The cells of the oxaliplatin group were stimulated with 1 μg/mL of oxaliplatin for 3 hours; the cells of the oxaliplatin and syringaresinol group were treated with syringaresinol at different concentrations (1 μg/mL, 10 μg/mL, and 100 μg/mL) for 1 hour and then stimulated with 1 μg/mL oxaliplatin for 3 hours, and the cells of the syringaresinol group were treated with 100 μg/mL of syringaresinol for 1 hour.

Thereafter, proteins were isolated from the cells of each treatment group. For protein isolation, 50 μL of a protein lysis buffer (pH 7.9, with 1.5 mM $MgCl_2$, 10 mM KCl) was added, followed by incubation at 4° C. for about 1 hour. The isolated proteins were quantified for each subject by using the Bradford (Bio-rad, USA) method using bovine serum albumin (BSA, Sigma, USA), and then 20 μg of the proteins were separated by 10% sodium dodecyl sulfate—polyacrylamide gel electrophoresis (SDS-PAGE) and transferred to polyvinylidene difluoride (PVDF) membranes (membrane, Gendepot, UK). The PVDF membranes were blocked in 5% skimmed milk (BD, USA) for 1 hour. The membranes were washed with a mixture of Tris-Buffered Saline and Tween 20 (TBST) and then incubated with primary antibodies (rabbit anti-iNOS, rabbit anti-phospho-extracellular signal-regulated kinase 1/2(p-ERK), rabbit anti-phospho-nuclear factor kappa B (p-NF-κB), and rabbit anti-GAPDH) diluted 1:1, 000 in 3% BSA, at 4° C. for one day, and then washed with TBST for 10 minutes three times, and incubated with secondary antibody at room temperature for 1 hour. After the secondary antibody incubation, washing with TBST was conducted, and then bands were identified by the ECL system (Santacruz, USA). The protein identification and quantitative analysis were performed using an imaging system (ChemiDoc XRS+ System, Bio-Rad).

All of the results were analyzed using the SPSS 21.0 package (SPSS Inc., Chicago, USA), and the experimental results were presented as the mean±standard deviation values. Statistical significance was validated using one-way analysis of variance (ANOVA) and then analyzed by Fisher's LSD test, and the significance probability value (p-value) was recognized only when $p<0.05$ and $p<0.01$.

As a result, the protein expression of inducible nitric oxide (iNOS), a representative enzyme involved in the inflammatory response, was significantly increased by oxaliplatin (1 μg/mL), but such an increase was significantly inhibited by syringaresinol (10 μg/mL and 100 μg/mL) (FIGS. 4A and 4B). Also, the degrees of activation of mitogen-activated protein kinases (MAPKs) and nuclear factor kappa-light-chain-enhancer of activated B (NF-κB), which are major signaling mechanisms involved in the inflammatory response, were investigated. The protein expression levels of p-ERK MAPK and p-NF-κB were significantly increased by oxaliplatin, but such an increase was significantly inhibited by syringaresinol (10 μg/mL and 100 μg/mL) (FIGS. 4A, 4C, and 4D). These results confirmed that the inflammatory response due to oxaliplatin can be inhibited by suppressing the signal mechanisms of ERK and NF-κB.

Based on the above description, it will be understood by those skilled in the art that the present disclosure may be implemented in a different specific form without changing the technical spirit or essential characteristics thereof. Therefore, it should be understood that the above embodiments are not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. A method for treatment of neuropathic pain, the method comprising administering to a subject with a pharmaceutical composition comprising as an active ingredient syringaresinol or a pharmaceutically acceptable salt thereof, wherein the neuropathic pain is allodynia caused by an anticancer drug or a pain caused by peripheral nerve injury.

2. The method of claim 1, wherein the allodynia is at least one selected from the group consisting of cold allodynia and mechanical allodynia.

3. The method of claim 1, wherein the anticancer drug is at least one anticancer drug selected from the group consisting of taxane- and platinum-based anticancer drugs.

4. The method of claim 3, wherein the anticancer drug is at least one selected from the group consisting of paclitaxel and oxaliplatin.

5. The method of claim 1, wherein the composition is orally administered at a concentration of 5 mg/kg to 100 mg/kg.

6. The method of claim 1, wherein the method further comprises administering to a subject a composition containing an anticancer drug as an active ingredient.

7. The method of claim 6, wherein the routes and frequencies of administration of the pharmaceutical composition comprising as an active ingredient syringaresinol or a pharmaceutically acceptable salt thereof and the composition containing an anticancer drug as an active ingredient are independent, respectively.

* * * * *